(12) United States Patent
Burres

(10) Patent No.: US 6,471,712 B2
(45) Date of Patent: Oct. 29, 2002

(54) DERMABRASION AND SKIN CARE APPARATUS

(76) Inventor: Steven A. Burres, 465 North Roxbury, Beverly Hills, CA (US) 90210

( * ) Notice: Subject to any disclaimer, the term of this patent is extended or adjusted under 35 U.S.C. 154(b) by 0 days.

(21) Appl. No.: 09/789,968

(22) Filed: Feb. 21, 2001

(65) Prior Publication Data
US 2002/0107527 A1 Aug. 8, 2002

Related U.S. Application Data
(60) Provisional application No. 60/238,167, filed on Oct. 5, 2000.

(51) Int. Cl.$^7$ ............................................. A61B 17/50
(52) U.S. Cl. ...................................... 606/131; 606/133
(58) Field of Search ................................ 606/131, 133; 15/104.93, 104.94, 229.12, 229.13, 229.11, 209.1; 132/76.4, 75.3, 75.8, 73.6; 51/295, 296

(56) References Cited

U.S. PATENT DOCUMENTS

| | | | | |
|---|---|---|---|---|
| 1,482,837 A | * | 2/1924 | Buck | 132/73.6 |
| 5,171,315 A | * | 12/1992 | Cabrero | 606/131 |
| 5,261,919 A | * | 11/1993 | Niedertscheider | 606/133 |
| 5,849,018 A | * | 12/1998 | Rosson et al. | 606/133 |
| 6,017,351 A | * | 1/2000 | Street | 606/313 |
| 6,062,229 A | * | 5/2000 | Kandratavich et al. | 132/73.6 |
| 6,165,182 A | * | 12/2000 | Caric et al. | 606/133 |
| 6,234,180 B1 | * | 5/2001 | Davis et al. | 132/74.5 |

* cited by examiner

Primary Examiner—Pedro Philogene
(74) Attorney, Agent, or Firm—Robert D. Buyan; Stout, Uxa, Buyan & Mullins, LLP

(57) ABSTRACT

Methods and apparatus for abrading, cleaning, massaging, buffing or otherwise treating the skin, fingernails, toenails or other body surfaces. The basic apparatus comprises a small motor mounted within a hand held housing and a cylindrical member rotatably mounted on the housing. The cylindrical member is rotatably driven by the motor and is covered with a treatment-effecting covering such as abrasive material, cloth, brush bristles, adhesive, massaging projections, etc. The cylindrical member may be placed in contact with the skin, nails or other body surface while rotating, thereby abrading, cleaning, massaging, buffing or otherwise treating the skin, nails or other body surface. In a more advanced embodiment, the device may incorporate a suction apparatus for suctioning away severed particles of skin or other matter. In either embodiment, the device may incorporate a drag for causing the rotation of the cylinder to stop when a predetermined maximum pressure is applied by the cylinder on the underlying body surface, thereby avoiding excessive abrasion or injury to the skin or other body surface being treated.

13 Claims, 2 Drawing Sheets

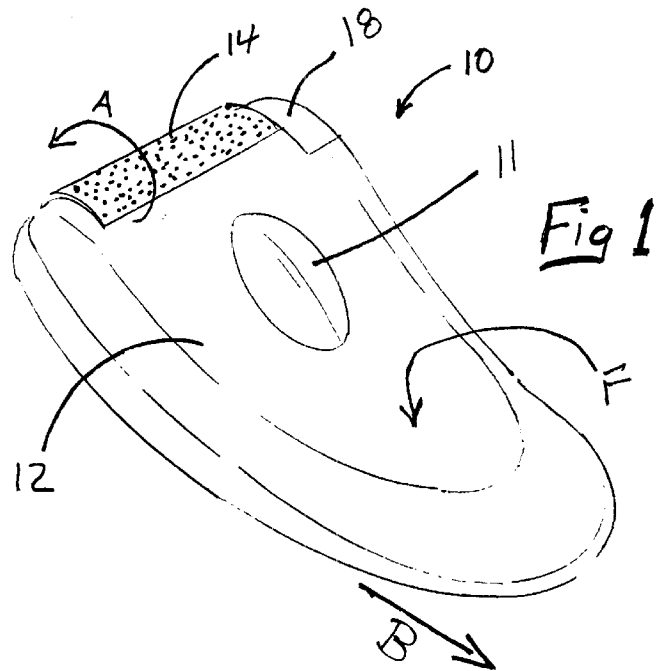
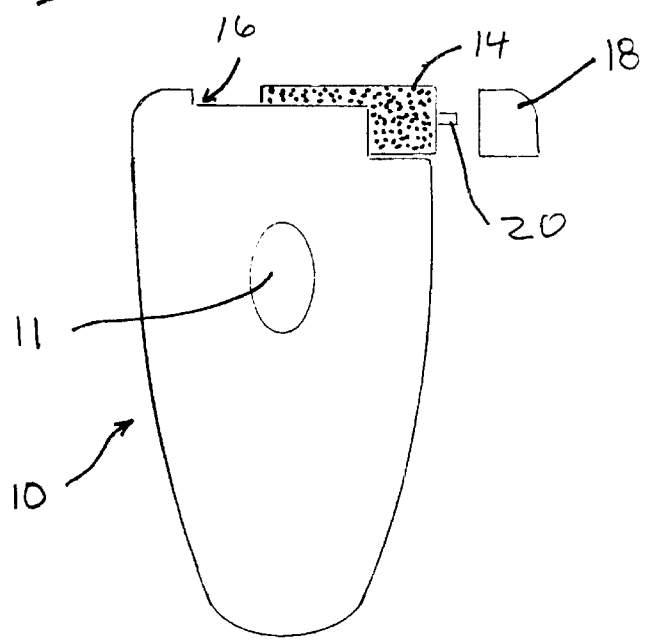
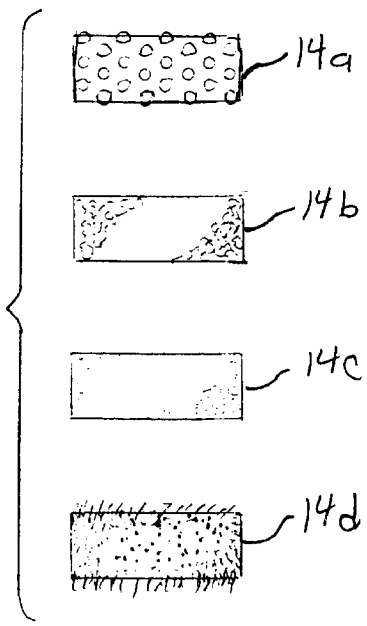

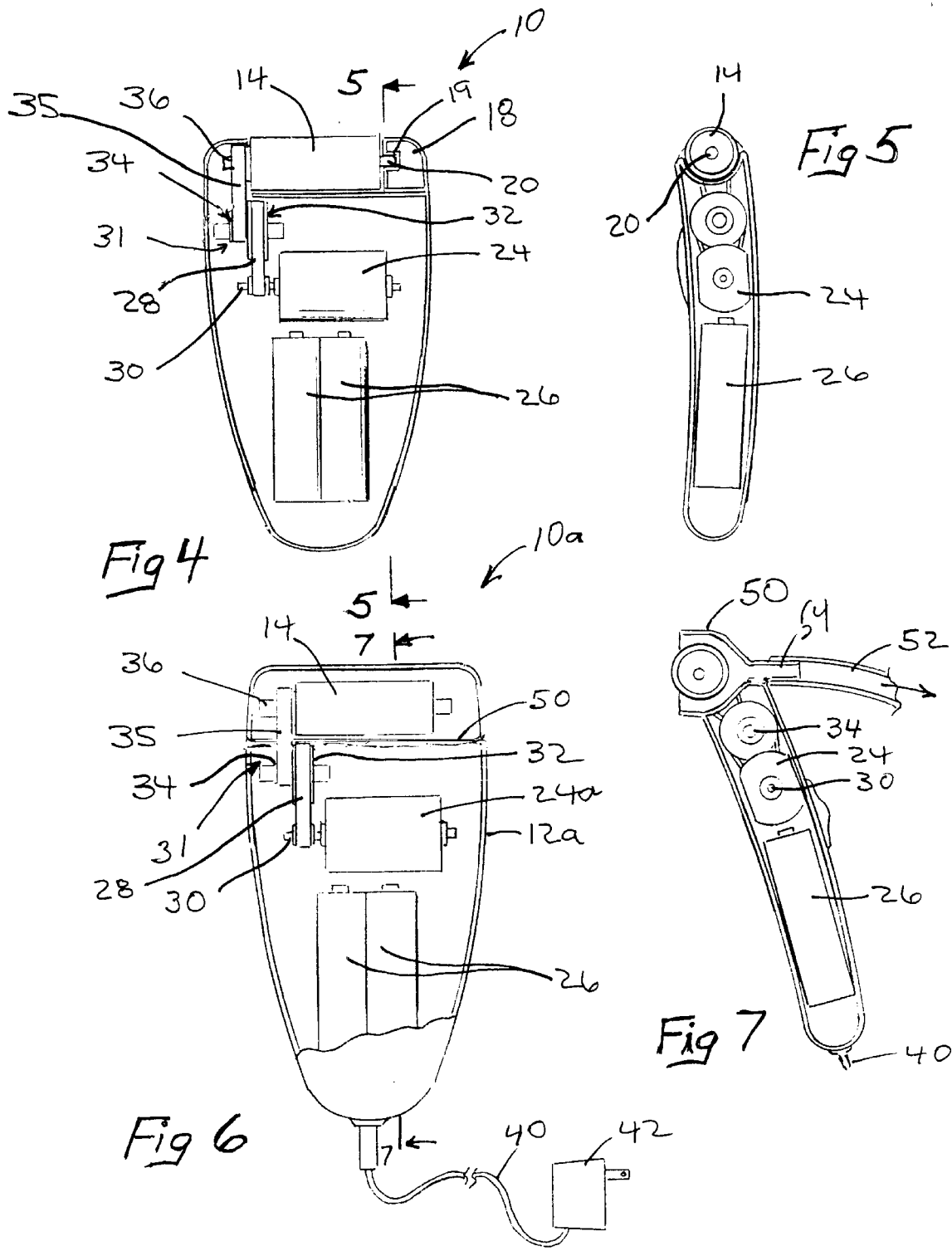

DERMABRASION AND SKIN CARE APPARATUS

RELATED APPLICATION

This application claims priority to United States Provisional Patent Application Ser. No. 60/238,167 entitled Dermabrasion and Skin Care Apparatus filed on Oct. 5, 2000, the entire disclosure of such provisional application being expressly incorporated herein by reference.

FIELD OF THE INVENTION

This invention relates generally to medical/cosmetological devices and methods, and more particularly to devices and methods for performing dermabrasion procedures.

BACKGROUND OF THE INVENTION

The human skin consists of three layers. The Epidermis or outer layer provides protection from the environment. The Dermis or middle layer primarily acts to provide structure and support. The third layer, which is the Subcutaneous Fat layer provides insulation and acts as a shock absorber.

The Epidermis is divided into three sublayers, the outermost of which is the Stratum Cornium. The Stratum Cornium consists of several layers of dead squamous cells and varies in thickness depending on location on the body. In certain disease states like eczema and psoriasis the stratum cornium may become abnormally thick and can cause irritation to the peripheral nerves and other skin components. The Stratum cornium tends to thicken as a result of age, sun exposure or other environmental exposure thereby resulting in the formation of wrinkles and creases. The formation of wrinkles or creases due to thickening of the Stratum Cornium can be attenuated somewhat by techniques known as exfoliation, dermabrasion or dermaplaning. In each of these techniques, all or a portion of the Stratum Cornium is removed.

Mild exfoliation can be accomplished by simply scrubbing the skin with a brush, terry cloth or particulate abrasive such as pumice. More aggressive exfoliation is typically performed by topical application of a chemical exfoliating agent (i.e., a "chemical peel"). Exfoliation typically removes only a portion of the Stratum Cornium and is useful in lessening fine lines and small wrinkles. Some chemical exfoliation procedures, such as those using alpha-hydroxy acids in relatively low concentrations, can be carried out at home or by a cosmetologist. More extensive "chemical peel" procedures are typically performed by physicians.

Dermaplaning is a technique wherein a device known as a dermatome is used to cut away a surface layer of skin. Dermatomes use sharp, precisely positioned cutting blades to remove predetermined thicknesses of skin. Because the amount of skin to be removed varies, the professional skill and judgment of a physician skilled in dermaplaning is typically required.

Dermabrasion is a technique wherein controlled surgical scraping is used to remove substantially all of the Stratum Cornium in one or more specific regions of the body. Dermabrasion is effective in removing some age related wrinkles or creases and can be used to soften the sharp edges of surface irregularities, giving the skin a smoother appearance. In addition to use in removing age related wrinkles and creases dermabrasion is often performed by physicians to improve the appearance of skin that has been scarred by trauma or prior surgery. The dermabrasion devices of the prior art have typically been designed such that an abrasive pad or disc is rotated about an axis that is generally perpendicular to the skin surface and the disc or pad is placed in contact with the skin while moving to abrade the surface of the skin. Because it is undesirable to remove too much skin during the dermabrasion process, skilled operator technique has been required to avoid excessive abrasion of the patient's skin. The application of slightly excessive force on the dermabraider during the procedure can result in over-abrasion of the skin (e.g., removal of the entire epidermis). For this reason, most dermabrasion devices have been relatively sophisticated and costly devices which are marketed primarily to physicians. Also, for this reason and possibly others, most dermabrasion procedures have heretofore been performed by physicians, despite the fact that if the amount of skin removed during the dermabrasion procedure is appropriately limited the procedure is extremely safe and could otherwise be performed on one's self at home or by a cosmetologist.

In view of the foregoing, there exists a need in the art for the design and development of a simple, relatively inexpensive dermabrasion device that a) can be used with minimal training by consumers and cosmetologists as well as more highly trained medical personnel and b) is equipped to minimize the likelihood of over abrading or injuring the skin.

SUMMARY OF THE INVENTION

The present invention provides simple, relatively inexpensive dermabrasion devices that can be used with minimal training by untrained consumers and cosmetologists or, in some cases, by physicians and other trained professionals. The dermabrasion devices of the present invention generally comprise a) a housing sized and configured to be grasped by a human hand; b) a motor disposed within the housing; c) a body-contacting cylinder rotatably mountable on said housing such that one side of the cylinder may be placed in contact with the body (e.g, skin surface, nail surface, tongue, etc.); and, a drive system connecting the motor to the body-contacting cylinder such that the motor will cause the cylinder to rotate while the cylinder is in contact with the patient's body (e.g, the skin, nails or tongue). The body contacting cylinder may be removable and interchangeable, and a variety of different cylinders may be provided, each such cylinder having a different surface covering suitable for a different purpose. For example, body-contacting cylinders may be covered with: abrasives such as diamond fragments or sandpaper for dermabrasion, corrugated rubber for small bumps or massaging, terry cloth for cleaning or buffing, an adhesive for removing dead cells or other particulate matter and/or a brush for brushing, buffing or the like. The motor may be powered by batteries, rechargeable batteries or by an electrical power cord connected to a power outlet.

Further in accordance with the invention, the body-contacting cylinder may, in at least some embodiments, be mounted in a recessed cavity or slot formed in the device housing such that only one side of the rotating cylinder is exposed for contact with the patient's skin or other body part. Also, in at least some embodiments, the body-contacting cylinder rotate about an axis that is parallel (or nearly parallel) to the skin or other body surface with which the rotating body-contacting cylinder is placed in contact. This partial shielding of the rotating cylinder and/or the fact that the cylinder rotates about an axis that is parallel to the patient's skin or body surface is/are in contrast to prior devices that employ a brush or disc that rotates about an axis that is generally perpendicular to the skin or body surface against which the brush or disc is compressed. These aspects of the invention, whether employed separately or concurrently, facilitate the use of smooth, controlled contact between the flat surface of the rotating body-contacting cylinder and the patient's skin or other body surface. This smooth, controlled contact deters or prevents the user from holding the device at an angle that would cause the ends or corners of the rotating body-contacting member to dig in or press into the patient's skin or body surface. Also, in this regard, the device of the present invention has minimal if any potential to cause damage to the skin or other body surface due to the user holding the device at an incorrect angle or otherwise applying uneven contact between the rotating body-contacting cylinder and the patient's skin or other body surface.

Further in accordance with the invention, there are provided devices of the foregoing character that include a suction housing that is connectable to a source of negative pressure and is configured and positioned relative to the body-contacting cylinder such that liberated particles, fragments, debris, liquid or other matter may be suctioned away during use of the device.

Still further in accordance with the invention, the device may be equipped or designed such that, when the abrasive force being applied to the body by the body-contacting cylinder exceeds a predetermined maximum, the body contacting cylinder will stop rotating, thereby avoiding over-abrasion or injury to the skin, nails, tongue or other body part. One way to achieve this is to design the drive train such that the body-contacting cylinder will stop rotating whenever the drag on the cartridge exceeds a predetermined amount, thereby preventing over-abrasion or injury.

BRIEF DESCRIPTION OF THE DRAWINGS

FIG. 1 is a perspective view of a first embodiment of a dermabraider device term of the present invention.

FIG. 2 is a partially disassembled front elevational view of the dermabraider device all of FIG. 1.

FIG. 3 shows a series of interchangeable body contacting cylinders usable in connection with the dermabraider devices of the present invention.

FIG. 4 is a front elevational view of the device of FIG. 1, wherein the housing cover has been removed exposing the interior components of the device.

FIG. 5 is a longitudinal sectional view through line 5—5 of FIG. 4, after the housing cover has been replaced.

FIG. 6 is a front elevational view of a second embodiment of a dermabraider device of the present invention, wherein the housing cover has been removed exposing the interior components of the device.

FIG. 7 is a longitudinal sectional view through line 7—7 of FIG. 6.

DETAILED DESCRIPTION OF EXEMPLARY EMBODIMENTS

The following detailed description and the drawings to which it refers are provided for the purpose of describing and illustrating certain examples and embodiments of the invention and are not intended to exhaustively describe all possible examples and embodiments of the invention. Indeed, this detailed description is not intended to limit the scope of the invention anyway.

A. Dermabrasion/Skin Care Devices

In the accompanying drawings, FIGS. 1–5 are directed to a first embodiment of a dermabraider device 10 while FIGS. 6–7 are directed to a second embodiment of a dermabraider device 10a.

A relatively simple dermabraider device 10 shown in FIGS. 1–5 comprises a housing 12 that is sized and configured to be grasped and held in a human hand, a cylindrical body-contacting member 14 rotatably mounted on one end of the housing 12, as shown, and an electric motor 24 positioned within the housing 12. This motor 24 is connected by way of a drive train 31 to a drive member 36 which rotatably drives the body-contacting cylindrical member 14, as can be seen in FIGS. 4 and 5. An on/off switch 11 is located on the frontal aspect of the housing 12 and may be finger-depressed to switch the motor 24 on and off, thereby starting and stopping the rotation of the body-contacting member.

In some embodiments, the cylindrical body contacting member 14 may be removable and interchangeable with alterative cylindrical body contracting members 14a, 14b, 14c, 14d as shown in FIGS. 2 and 3. To facilitate removal a changing of the cylindrical body contacting member 14, a removable segment 18 may be formed in the housing 12 adjacent one end of a cavity 16 within which the cylindrical body contacting member 14 is mounted. When it is desired to remove or change the cylindrical body contacting member 14, the removable housing segment 18 may be disconnected from the remainder of the housing 12 and the cylindrical body contacting member 14 and accompanying axle 20 may be extracted laterally and removed from the device 10. Thereafter, that cylindrical body contacting member 14 may be separated from the reusable axle and discarded. A replacement cylindrical body contacting member may then be positioned on the axle 20 and the new cylindrical body contacting member and axle combination may then be reinserted into the receiving cavity 16 such that one end of the axle 20 engages the drive member 36. The removable segment 18 of the housing may then be replaced such that the free end of the axle 20 is rotatably received within idler notch formed in the inner aspect of the removable housing segment 18, as shown in FIG. 4. This removeability and interchangeably of the cylindrical body contacting member 14 may be used simply to replace a worn out cylindrical body contacting member with a new one or it may be used to replace one cylindrical body contacting member 14 (such as one having an abrasive covering) with a different type of cylindrical body member 14a, 14b, 14c or 14d (having a different type of covering) so that a different procedure (e.g, nail buffing, tongue brushing, make-up removal) may be performed. In this regard, one body contacting member 14 may be covered with an abrasive while another cylindrical body contacting member 14a may be covered with an elastomeric material that has raised surface projections (e.g., bumps or ribs) formed thereon so as to be useable for massaging the skin or a body surface. Another cylindrical body contacting No. 14b may be covered with a cloth material (e.g., terry cloth) so as to be usable for cleaning the body surface or applying/removing substances such as make-up, cold cream, emollients, etc. Another cylindrical body contacting member 14c may be covered with an adhesive which will adhere to particles of skin, dust or other foreign matter so as to remove such matter from the skin or other body surface. Another cylindrical body contacting member 14d may be covered with brush bristles for scrubbing or brushing the dermal surface, nails, tongue, etc.

In the particular embodiment showed FIGS. 1–5, the motor 24 comprises a 1.27 watt output, 3.0 volt, DC motor of the type commercially available as Model FF180PH2852 from Mabushi Motors of New Jersey. This motor 24 is driven by two AA batteries 26 which are mounted within the housing 12, as shown. The drive train 31 comprises a first belt 28 which links the motor shaft 30 to a first pulley 32, and a second belt 35 which links a second pulley 34, which is mounted on the same axle as the first pulley 32 but which is smaller in diameter than the first pulley 32, to the drive member of 36. In this manner, when the motor 24 is energized, rotation of the motor shaft 30 will cause the first pulley 32 to be rotated by belt 28, with concurrent rotation of the smaller diameter second pulley 34. The rotation of the second pulley causes the second belt 35 to rotatably drive the drive member 36. The axle 20 of the cylindrical body contacting member 14 is inserted within the drive member 36 such that when the drive member 36 rotates, so will the axle 20 and accompanying cylindrical body member 14. In this regard, the cylindrical body contacting member 14 is mounted on the axle 20 in a rigid fashion such that it will not slip or separate and will rotate concurrently with the axle 20.

One or both belts 28, 35 may be sized and designed to slip whenever the drag on the cylindrical body-contacting member 14 and the resultant resistance to rotation of pulleys 34 and 36 exceeds a predetermined maximum amount. For example, the system may be designed such that the application of 540–660 grams per centimeter of force will cause the rotation of the cylindrical body-contacting member 14 to stop.

In a typical dermabrasion application of this first embodiment of the device 10, the user will wash and dry his or her skin in the area to be treated. The device housing 12 is grasped in the user's hand and the on/off switch 11 is depressed, thereby switching on the motor 24 and causing the cylindrical body member 14 covered with an abrasive material such as sandpaper, to rotate in the direction of arrow A shown in FIG. 1. With the front surface F of the device 10 in direct juxtaposition to the skin surface being treated, the user holds the device 10 such that the rotating cylindrical body contacting member 14 makes contact with the skin in the area to be treated. As the rotating cylindrical body member 14 remains in contact with the skin, the device 10 is slowly moved in the direction of arrow B on FIG. 1, thereby pulling the rotating cylindrical body contacting member 14 across the surface of the patient's skin in a direction that is substantially opposite the direction in which the cylindrical body-contacting member is rotating. This sweeping movement may then be repeated a number of times until the skin appears pink or in accordance with instructions provided by a physician or by the manufacture of the device. Typically, depending on the coarseness of the abrasive surface of the cylindrical body contacting member 14, one to five passes over the surface of the skin will be adequate for each treatment. This may, however, vary depending on the coarseness of the abrasive surface used, the thickness or elasticity the patient's skin and other variables. Similar technique may also be employed for massaging, buffing, removing particulate matter, brushing or other applications using alternative cylindrical body contacting members, examples of which are shown in FIG. 3 and described hereabove.

A second embodiment of a dermabraider device 10a is shown in FIGS. 6 and 7. This second embodiment of the device 10a comprises a housing 12 that contains substantially the same internal components, including one or more batteries 26, a motor 27 and a drive train 31, as the above-described first embodiment of the device 10. However, this second embodiment 10a may be more suited to professional use and incorporates a suction housing 50 which partially surrounds the rotatable body contacting member 14. Also, in this embodiment of the device 10a, the batteries 26 may be of a rechargeable type and, when not in use, the device 10a may be attached to an electrical current outlet by way of power cord 40 and adapter 42, so as to re-charge the batteries 26. A suction tube 52 may be attached to suction port 54 off suction housing 50, and the opposite end of such suction tube 52 may be connected to a negative pressure source, such as an in-wall suction port commonly found in most hospital or surgical center operating rooms. Also, in this advanced embodiment of the device 10a, the body contacting member 14 may be covered with a relatively coarse abrasive material, such as diamond particles or fragments for more aggressive dermabrasion than would typically be performed using the first embodiment 10 of the device, which is designed primarily for personal use.

It is to be appreciated that any or all of the individual elements or components of the basic device 10 may be incorporated into the advanced device 10a, and vice versa. Thus, many hybrid embodiments may be formed incorporating selected elements or components from both the basic device 10 and advanced device 10a.

B. Dermabrasion/Skin Care Methods

The device shown in FIGS. 1–5 is particularly suited to use by persons who do not possess formal medical, surgical or cosmotological training.

In a typical home-use dermabrasion procedure performed using the device of FIGS. 1–5, the area of skin to be treated is initially washed with an antimicrobial wash or plain soap and water and allowed to dry. The removable segment 18 of the device housing 12 is removed. A sandpaper-covered dermabrasion cylinder 14 is mounted on an axle 20 and the cylinder/axle combination 14/20 is inserted into the receiving cavity 16 such that one end of the axle 20 engages the drive member 36 so as to be rotatably driven thereby. The removable segment 18 is then replaced such that the other end of the axle 20 is rotatably inserted within the idler notch formed within the inner aspect of the removable segment 18.

Thereafter, the device 10 is grasped in the user's hand and is held such that the front F of the housing 12 is juxtaposed to the user's skin. The on/of switch 11 is depressed, thereby energizing the motor 24 and causing the sandpaper-covered cylinder 14 to rotate in direction A (see FIG. 1). The user then touches the rotating cylinder 14 against one edge of the area of skin to be abraded and, while maintaining contact between the rotating cylinder 14 and the skin, slowly moves the device 10 in the direction of arrow B (see FIG. 1). This causes the rotating cylinder 14 to be moved over the surface of the skin in a direction (arrow B) opposite the direction in which the cylinder 14 is rotating (arrow A). After the rotating cylinder has reached the opposite edge of the area of skin to be abraded, the user lifts the rotating cylinder 14 away from contact with the skin, moves the device 10 and once again places the rotating cylinder 14 into skin contact at the first edge of the skin area being treated. The above-set-forth procedure is then repeated a number of times until the desired area of skin has been treated. The number of passes made over each skin area depends on the roughness of the sandpaper covering of the particular cylinder 14 being used and the amount of stratum cornium that the user wishes to remove. Typically, 2 or 3 passes over each skin area may be carried out in each treatment. After the treatment has been completed, the on/off switch 11 is once again depressed, thereby de-energizing the motor 24 and stopping the rotation of the cylinder 14. The treatment may be repeated on a daily or weekly basis for routine skin care or if and when the wrinkles or thickened skin reappear.

As discussed hereabove, the tension(s) of one or both of the belts 28, 35 that drive the cylinder 14 is/are set to slip if the user presses the rotating cylinder 14 against the skin too vigorously or if the drag on the rotating cylinder 14 otherwise exceeds a predetermined maximum amount. Thus, if the maximum allowed pressure of the rotating cylinder 14 against the skin is exceeded, one or both of the the belts 28, 35 will slip and the cylinder 14 will cease to rotate. In this manner, the user is prevented from over-abrading or substantially injuring the skin.

Procedures other than dermabrasion may be carried out in a fashion similar to the above described dermabrasion procedure, using other cylindrical members 14a, 14b, 14c, 14d in place of the sandpaper-covered dermabrasion cylinder 14. For example, the massage cylinder 14a shown in FIG. 3 may be installed in the device 10 and used in the above-described manner for massaging the skin. The cloth covered massage cylinder 14b shown in FIG. 3 may be installed in the device 10 and used in the above described manner for cleaning the skin, removing make-up or buffing the fingernails or toenails. The adhesive cylinder 14c shown in FIG. 3 may be installed in the device 10 and used in the above-described manner for removing particles or dry flakes from the skin. Or, the brush-covered cylinder 14d shown in FIG. 3 may be installed in the device 10 and used in the above-described manner for buffing the fingernails or toenails, for scrubbing the skin or for massaging the skin. Other types of coverings may also be used on the cylinders to accomplish other procedures or methods.

The advanced device 10a shown in FIGS. 6–7 may be used by a physician or other trained professional in substantially the same manner as described hereabove with respect to the basic device 10. However, the cylindrical members 14 used with the advanced device 10a may be covered with materials or surface treatments that differ from those used with the basic device 10, to facilitate the intended professional use of the advanced device 10a. For example, in this regard, dermabrasion cylinders 14 intended for use with the basic device 10 may be covered with sandpaper while dermabrasion cylinders 14 intended for use by trained professionals with the advanced device 10a may be covered with sandpaper of greater coarseness.

It is to be understood and appreciated that the invention has been described herein with reference to certain presently preferred embodiments and examples only, and no effort has been made to exhaustively describe all possible embodiments and examples of the invention. Indeed, as those skilled in the art will appreciate, various additions, deletions, modifications and variations may be made to the particular embodiments and examples described hereabove without departing from the intended spirit and scope of the invention. Accordingly, it is intended that all such additions, deletions, modifications and variations be included within the scope of the following claims.

I claim:

1. A apparatus for dermabrasion and skin care in a human or animal subject, said apparatus comprising:
    a housing sized and configured to be grasped by a human hand;
    a motor disposed within said housing;
    at least one cylinder having a body treatment-effecting outer surface, said at least one cylinder being roatably mountable on or in the housing such that its treatment-effecting outer surface may be placed in contact with the skin of the patient; and,
    a drive system for connecting the motor to one of said cylinders when that cylinder is on the housing while its treatment-effecting outer surface is in contact with the skin;
    said apparatus being constructed such that said cylinder mounted on the apparatus will automatically stop rotating when the drag on the cylinder exceeds a predetermined maximum amount.

2. Apparatus according to claim 1 wherein the at least one cylinder comprises a variety of cylinders that are interchangeably mountable on the housing, each of said cylinders having a different treatment-effecting outer surface.

3. Apparatus according to claim 2 wherein the cylinders have treatment-effecting surfaces selected from the group consisting of:

mildly abrasive surface for mild dermabrasion;

moderately abrasive surface for moderate dermabrasion;

highly abrasive surface for deep dermabrasion;

a skin cleansing surface;

a cloth surface;

a massaging surface;

a ribbed elastomeric surface; and, a brush surface.

4. Apparatus according to claim 1 wherein the motor is battery driven.

5. Apparatus according to claim 1 wherein the drive system comprises a belt drive having a belt that slips when the drag on the cylinder exceeds the predetermined maximum, such slippage of the belt being effective to substantially stop the rotation of the cylinder so long as the drag on the cylinder continues to exceed the predetermined maximum amount.

6. Apparatus according to claim 1 wherein a cavity is formed in the housing and the cylinder is mounted at least partially within the cavity such that only a portion of the cylinder is exposed so as to be placeable in contact with the subject's body.

7. Apparatus according to claim 6 wherein cavity is formed such that the ends of the cylinder are substantially shielded by the housing such that the ends of the cylinder can not be placed in contact with the subject's body.

8. Apparatus according to claim 6 wherein the cavity is formed and the cylinder is mounted such that only a side surface of the cylinder may be placed in contact with the subject's body.

9. Apparatus according to claim 1 wherein the cylinder, when mounted on or in the housing, rotates about an axis of rotation and wherein the treatment-effecting surface of the cylinder is placeable in contact with a body surface that is generally parallel to the axis of rotation about which the cylinder rotates.

10. Apparatus according to claim 6 wherein the cylinder, when mounted within the cavity formed in the housing, rotates about an axis of rotation and wherein the cavity is sized and configured and the cylinder is positioned such that treatment-effecting surface of the cylinder may only be placed in contact with a body surface that is generally parallel to the axis of rotation about which the cylinder rotates.

11. A method for dermabrasion or skin care, said method comprising the steps of:
    (A) providing apparatus according to any of the preceding claims 1, 5;
    (B) mounting a desired cylinder on the housing;
    (C) holding the housing adjacent the subject's skin such that the cylinder is in contact with the skin; and,
    (D) energizing the motor so as to cause the cylinder to rotate while in contact with the skin so long as the amount of drag on said cylinder remains below said predetermined maximum amount.

12. A method according to claim 11 wherein the axis about which the cylinder rotates is substantially parallel to the skin surface being contacted by the cylinder during performance of Step D.

13. A method according to claim 11 wherein the method further comprises the step of:
    (E) moving the housing such that the rotating cylinder moves over the surface of the skin as it continues to rotate.

* * * * *